(12) United States Patent
O'Donnell

(10) Patent No.: US 11,131,614 B2
(45) Date of Patent: Sep. 28, 2021

(54) AUTONOMOUS COMPACTION TESTING SYSTEMS AND METHODS

(71) Applicant: Caterpillar Paving Products Inc., Brooklyn Park, MN (US)

(72) Inventor: Timothy M. O'Donnell, Long Lake, MN (US)

(73) Assignee: Caterpillar Paving Products Inc., Brooklyn Park, MN (US)

( * ) Notice: Subject to any disclaimer, the term of this patent is extended or adjusted under 35 U.S.C. 154(b) by 0 days.

(21) Appl. No.: 16/038,212

(22) Filed: Jul. 18, 2018

(65) Prior Publication Data

US 2020/0025662 A1  Jan. 23, 2020

(51) Int. Cl.
| | | |
|---|---|---|
| *G01N 9/36* | (2006.01) | |
| *G01N 33/24* | (2006.01) | |
| *E02D 3/02* | (2006.01) | |
| *E01C 21/00* | (2006.01) | |
| *G05D 1/02* | (2020.01) | |

(52) U.S. Cl.
CPC ............... *G01N 9/36* (2013.01); *E01C 21/00* (2013.01); *E02D 3/02* (2013.01); *G01N 33/24* (2013.01); *G05D 1/021* (2013.01)

(58) Field of Classification Search
CPC .......... G01N 9/36; G01N 33/24; E01C 21/00; E02D 3/02; G05D 1/021
See application file for complete search history.

(56) References Cited

U.S. PATENT DOCUMENTS

| | | | |
|---|---|---|---|
| 6,065,904 A | | 5/2000 | Cook et al. |
| 6,122,601 A | | 9/2000 | Swanson et al. |
| 9,366,529 B2 | | 6/2016 | Nakamura et al. |
| 2004/0039498 A1 | * | 2/2004 | Ollis .................... G05D 1/0274 701/23 |
| 2018/0179719 A1 | * | 6/2018 | Wisley .................... E02D 1/022 |

FOREIGN PATENT DOCUMENTS

| | | |
|---|---|---|
| CN | 203069444 | 7/2013 |
| CN | 103852575 | 6/2014 |
| JP | 2017207815 A * | 11/2017 |

OTHER PUBLICATIONS

Engllish machine translation of Ono (JP-2017207815-A) (Year: 2017).*
Ono (English machine translation of Ono (JP-2017207815-A) (Year: 2017).*

* cited by examiner

*Primary Examiner* — Bao Long T Nguyen
*Assistant Examiner* — Bakari Underwood
(74) *Attorney, Agent, or Firm* — Schwegman, Lundberg & Woessner

(57) ABSTRACT

An autonomous terrestrial compaction testing vehicle includes a compaction density meter coupled to the vehicle and a controller. The controller is communicatively connected to the compaction density meter and to a controller of a compactor machine that is compacting or has compacted an area of terrain. The controller is configured to autonomously control movement of the vehicle over the compacted area and control the compaction density meter to take a plurality of compaction density measurements at a plurality of locations of the compacted area.

22 Claims, 5 Drawing Sheets

AUTONOMOUS COMPACTION TESTING SYSTEMS AND METHODS

BACKGROUND

Compaction of a construction material is recognized as being important for improving the stability of the material in construction operations such as soils and asphalt pavement. By compacting the surface, soil strength and stability can be increased to the magnitude required by the design. State Highway Agencies and contractors are concerned about quality control of the quality and/or extent of compaction of various types of terrains. In some cases, state or other agencies may impose regulations on contractors with regard to the amount of compaction required for different types of terrains, including, as an example, asphalt roads or other asphalt applications. Thus, compacting an area of terrain may require the process of compacting the material in the area and also an additional step of testing the compacted area to determine if it meets applicable standards and/or regulations.

SUMMARY

In an example according to this disclosure, an autonomous terrestrial compaction testing vehicle includes a compaction density meter coupled to the vehicle and a controller. The controller is communicatively connected to the compaction density meter and to a controller of a compactor machine that is or has compacted an area of terrain. The controller is configured to: automatically control movement of the vehicle over the compacted area. The controller is also configured to control the compaction density meter to take a plurality of compaction density measurements at a plurality of locations of the compacted area, and send the plurality of compaction density measurements and the plurality of locations to the controller of the compactor machine.

In an example, a system includes a compactor work machine comprising a compactor controller and configured to compact an area of terrain, and an unmanned autonomous vehicle (UAV). The UAV includes a compaction density meter coupled to the UAV, and a UAV controller communicatively connected to the compaction density meter and to the compactor controller. The UAV controller is configured to autonomously control movement of the vehicle over at least a portion of the area of terrain that has been compacted by the compactor work machine, and control the compaction density meter to take a plurality of compaction density measurements at a plurality of locations of the compacted area.

In an example, a method includes compacting at least a portion of an area of terrain with a compactor work machine, moving, by a controller, an unmanned autonomous vehicle (UAV) over the at least a portion of the compacted area, and autonomously measuring, by the controller, a compaction density of the at least a portion of the compacted area at one or more locations with a compaction density meter coupled to the UAV and communicatively coupled to the controller.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
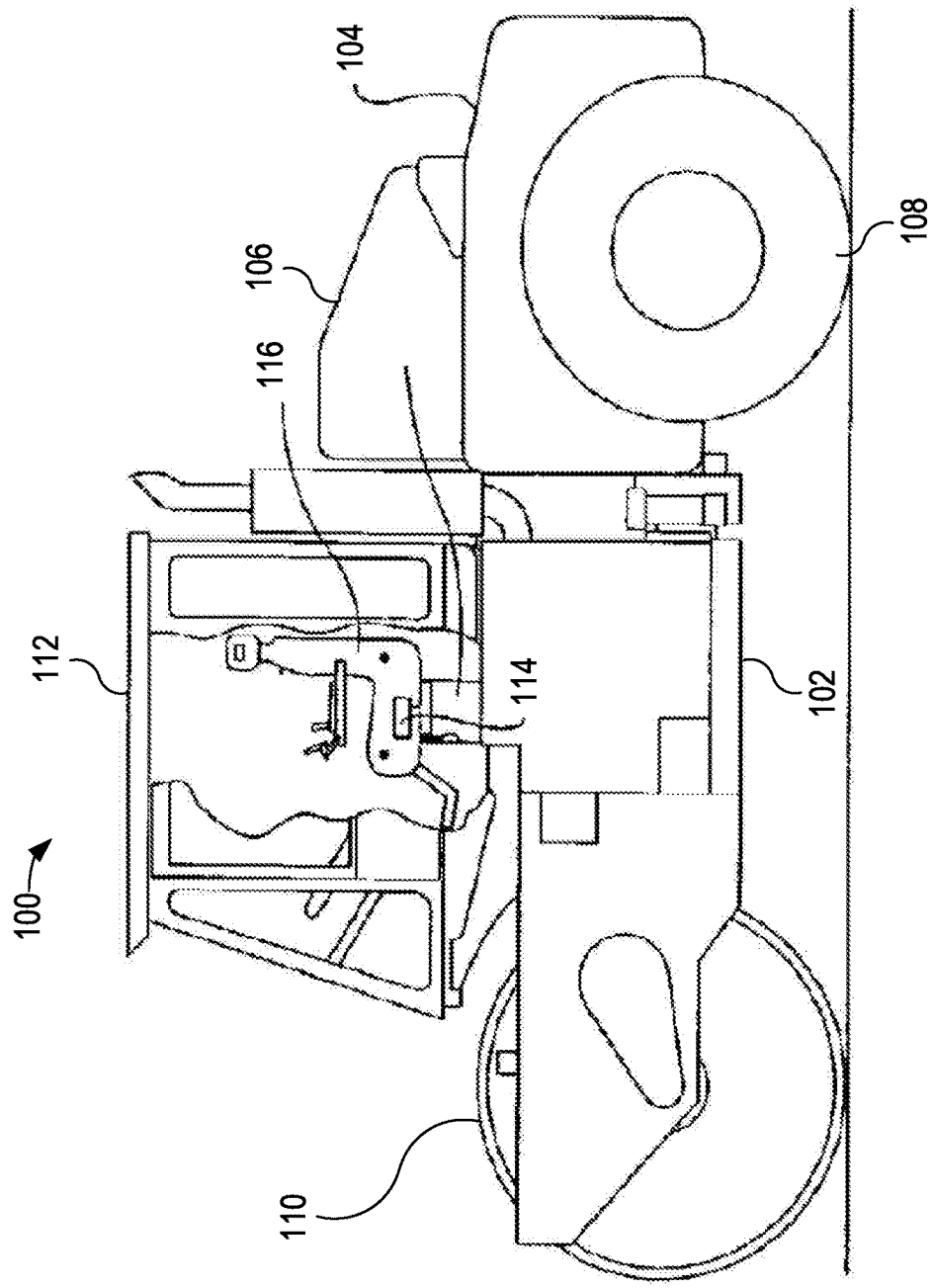
FIG. 1 depicts an example compactor work machine in accordance with this disclosure.
Figure 2:
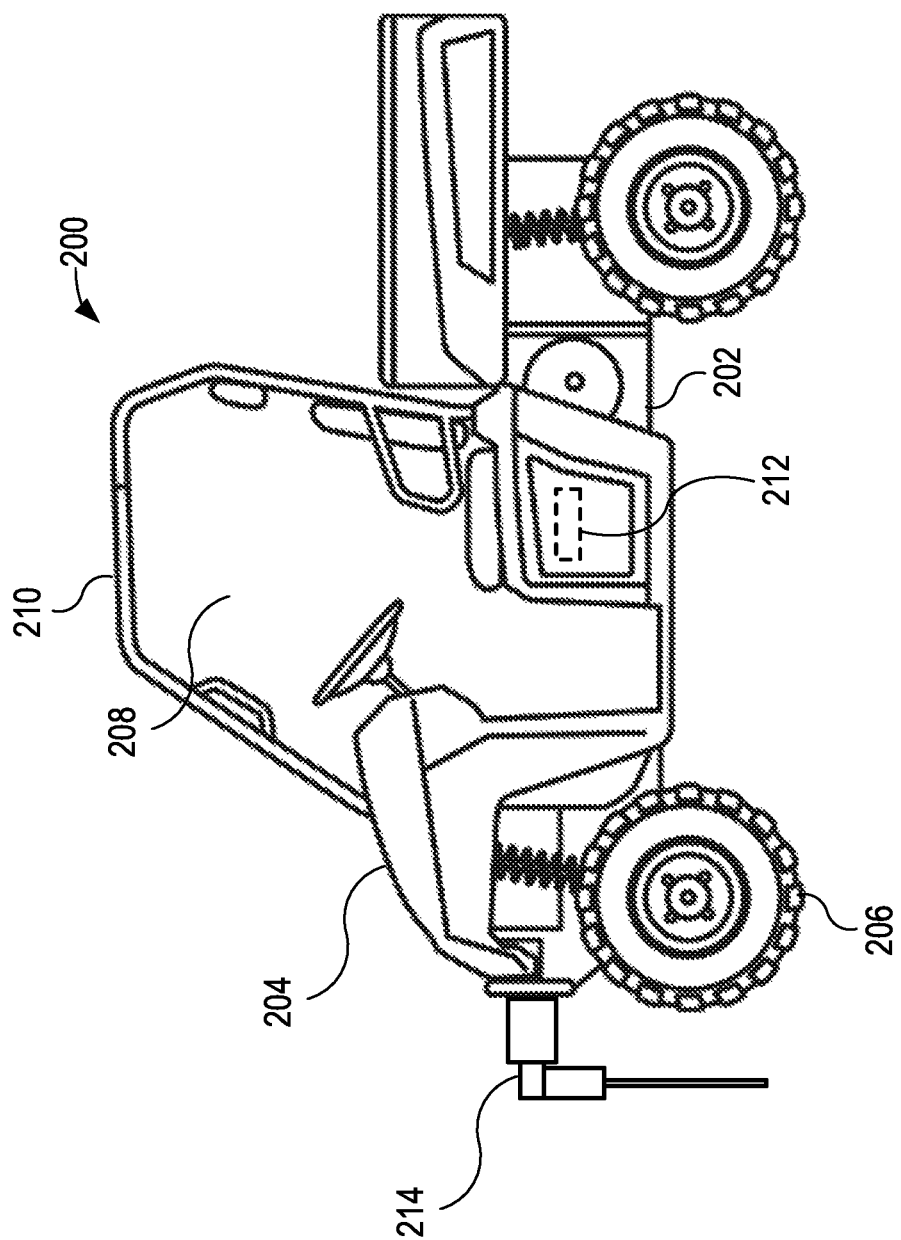
FIG. 2 depicts an example of an autonomous terrestrial vehicle in accordance with this disclosure.

FIGS. 1 and 2 depict a compactor work machine and an autonomous terrestrial vehicle (sometimes referred to as unmanned autonomous vehicle or UAV), respectively, which compactor and vehicle may operate in concert to process an area of terrain. In an example, the compactor work machine compacts a target area of asphalt and the autonomous vehicle autonomously traverses and measures compaction density of the compacted area in one or more locations.

FIG. 1 depicts example compactor work machine 100 in accordance with this disclosure. Machine 100 can be, for example, a vibratory drum compactor, which may be used to process various materials, including compacting asphalt. In FIG. 1, example machine 100 includes frame 102 to which body 104 is coupled, power generator 106, wheels 108, drum 110, cab 112, and controller 114. Although not depicted, machine 100 also includes brakes associated with and configured to limit and/or stop rotation of wheels 108.

Work machine 100 includes frame 102, to which body 104 of the machine is attached. Frame 102 can include one or more portions and/or separate frames coupled to one another. In an example, frame 102 includes multiple frames, which are coupled to and configured to articulate relative to one another.

Machine 100 also includes power generator 106, which is configured to generate power to propel the machine and which is operatively coupled to wheels 108. Power generator 106 can include various power generation platforms, including, for example, an internal combustion engine, whether gasoline or diesel, or an electric motor. Additionally, power generator 106 will commonly be operatively coupled to one or more drive train components, including, for example, a transmission, which are configured to transmit the power generated by power generator 106 to wheels 120. In addition to propelling machine 100 over various terrains, power generated by power generator 106 can be used for various operational requirements of the machine, including operating an implement attached thereto.

Drum 110 is coupled to and configured to rotate relative to frame 102 and machine 100. Drum 110 can provide static compaction force (i.e. weight caused by gravity) to process materials, as well as can be coupled to one or more mechanisms configured to vibrate the drum and thereby provide dynamic forces to improve compaction results. Drum 110 can be a number of different sizes, materials, weights, among other characteristics, depending upon the intended use of machine 100.

Example compactor 100 also includes a controller, which can be, as an example, an electronic control unit (ECU) 114. In the example of FIG. 1, ECU 114 is coupled to an operator seat 116 disposed in cab 112. Although ECU 114 is coupled to a seat 116 in the example of FIG. 1, in other examples the ECU could be positioned at different locations of machine 100. ECU 114 can include transmitter, receiver, transceiver, and other componentry configured to enable ECU 114 to communicate and exchange information, data, signals, as examples, with other systems and/or machines/vehicles.

An electronic control unit (ECU) can be an embedded system that controls machine electrical systems and/or other subsystems of the machine. Types of ECUs include Electronic/engine Control Module, Powertrain Control Module, Transmission Control Module, Brake Control Module, Suspension Control Module, among other examples. In the case of industrial, construction, and other heavy machinery, example ECUs can also include an Implement Control Module associated with one or more implements coupled to and operable from the machine.

The ECUs and other electronic controls of machine 100, including ECU 114 can include software, hardware, and combinations of hardware and software configured to execute a number of functions attributed to the components in the disclosed examples. The ECUs or other electronic controls of machine 100 can be an analog, digital, or combination analog and digital controllers including a number of components. As examples, the ECUs and other electronic controls of machine 100 can include integrated circuit boards or ICB(s), printed circuit boards PCB(s), processor(s), data storage devices, switches, relays, etcetera. Examples of processors can include any one or more of a microprocessor, a controller, a digital signal processor (DSP), an application specific integrated circuit (ASIC), a field-programmable gate array (FPGA), or equivalent discrete or integrated logic circuitry.

The ECUs and other electronic controls of machine 100 may include storage media to store and/or retrieve data or other information, for example, signals from sensors. Examples of non-volatile storage devices include magnetic hard discs, optical discs, floppy discs, flash memories, or forms of electrically programmable memories (EPROM) or electrically erasable and programmable (EEPROM) memories. Examples of volatile storage devices include random access memories (RAM), dynamic random access memories (DRAM), static random access memories (SRAM), and other forms of volatile storage devices. The data storage devices can be used to store program instructions for execution by processor(s) of, for example, ECU 114.

The ECUs and other electronic controls of machine 100 can be configured to communicate with one another and with other components of machine 100 via various wired or wireless communications technologies and components using various public and/or proprietary standards and/or protocols. Examples of transport mediums and protocols for electronic communication between components of machine 300 include Ethernet, Transmission Control Protocol/Internet Protocol (TCP/IP), 802.11 or Bluetooth, or other standard or proprietary transport mediums and communication protocols.

FIG. 2. depicts an example of an autonomous terrestrial vehicle 200 in accordance with this disclosure. Vehicle 200 can be, for example, a utility task vehicle (UTV), which is also referred to as a side-by-side, recreational off-highway vehicle, or multipurpose off-highway utility vehicle. More generally, vehicle 200 can be a number of different types of unmanned autonomous vehicles (UAVs). In FIG. 2, example autonomous vehicle 200 includes frame 202, power generator 204, wheels 206, open cab 208, rollover protection structure (RODS) 210, controller 212, and compaction density meter 214. Although not depicted, vehicle 200 also includes brakes associated with and configured to limit and/or stop rotation of wheels 206.

Controller 212 is configured to control operation of vehicle 200 autonomously by, as an example, executing one or more algorithms, programs, etcetera configured to control movement of the vehicle over various terrains. Controller 212 can include various components to autonomously control movement of vehicle 200, take compaction density measurements using compaction density meter 214, and communicate data, signals, information with another machine or system, including, e.g. a compaction work machine like machine 100 of FIG. 1. Controller 212 can, in examples, be configured to control compaction density meter 214 to take a plurality of measurements at a plurality of locations and to transmit the measurements and locations at which such measurements are taken to another device or system. In order to track the location of vehicle 200 and the locations of compaction density measurements, controller 212 can include, for example, a Global Positioning System (GPS).

Controller 212 of autonomous terrestrial vehicle 200 can include software, hardware, and combinations of hardware and software configured to execute a number of functions attributed to the components in the disclosed examples. Controller 212 can be an analog, digital, or combination analog and digital controller including a number of components. As examples, controller 212 can include integrated circuit boards or ICB(s), printed circuit boards PCB(s), processor(s), data storage devices, switches, relays, etcetera. Examples of processors can include any one or more of a microprocessor, a controller, a digital signal processor (DSP), an application specific integrated circuit (ASIC), a field-programmable gate array (FPGA), or equivalent discrete or integrated logic circuitry.

Controller 212 can include storage media to store and/or retrieve data or other information, for example, signals and/or measurement taken by compaction density meter 214. Examples of non-volatile storage devices include magnetic hard discs, optical discs, floppy discs, flash memories, or forms of electrically programmable memories (EPROM) or electrically erasable and programmable (EEPROM) memories. Examples of volatile storage devices include random access memories (RAM), dynamic random access memories (DRAM), static random access memories (SRAM), and other forms of volatile storage devices. The data storage devices can be used to store program instructions for execution by processor(s) of controller 212.

Controller 212 can be configured to communicate with other devices/systems, including, for example, a compaction work machine via various wired or wireless communications technologies and components using various public and/or proprietary standards and/or protocols. Examples of transport mediums and protocols for electronic communication between components of machine 300 include Ethernet, Transmission Control Protocol/Internet Protocol (TCP/IP), 802.11 or Bluetooth, or other standard or proprietary transport mediums and communication protocols.

In the example of FIG. 2, controller 212 is disposed in open cab 208 beneath a seat/bench. Although controller 212 is disposed in cab 208 in the example of FIG. 2, in other examples the controller could be positioned at different locations of machine 200.

Compaction density meter 214 is coupled (directly or indirectly) to frame 202 of autonomous vehicle 200. Meter 214 can include a variety of different types of compaction density measurement devices. In an example, compaction density meter 214 is a mechanical or electromechanical device, which is configured to drive a stake or rod into compacted soil, asphalt or another material and to measure the pressure/force required to drive the stake a prescribed distance into the material.

Compaction density meter 214 can include control, processing, memory and other hardware, software, and combinations thereof to control operation of the meter. Additionally, compaction density meter 214 and controller 212 can be communicatively connected (via a wired or wireless connection) and configured to exchange information, including, transmitting compaction density measurements taken by meter 214 to controller 212.

In an example, compactor work machine 100 and autonomous terrestrial vehicle 200 work in concert to process (e.g., compact) a target area of terrain and to measure and certify/validate the results of such processing by measuring compaction density of the processed target area of terrain in one or more locations. Compaction density standards or thresholds may be required by local city, county or state and/or federal regulations. In order to comply with such regulations, processing a target area of terrain, e.g., compacting an area of asphalt may require an additional step of measuring compaction density after one or more compaction runs by a compactor machine like machine 100.

Such compaction density measurements have commonly been executed manually by an operator positioning a compaction density meter at various locations of an area of terrain that has already been compacted and taking measurements and then comparing the measurements to thresholds or standards for compacted asphalt or other materials. In examples according to this disclosure, however, autonomous vehicle 200 is configured to automatically traverse an area of terrain that has been or is in the process of being compacted and to automatically take a plurality of compaction density measurements and transmit the measurements to another device or system, including, as examples, a stationary or mobile base station or another vehicle like compactor machine 100. In examples, vehicle 200 can be configured to take the compaction density measurements with meter 214 and can sample and send the measurements after a target area has been completely processed by compactor machine 100, or, alternatively, vehicle 200 can follow compactor 200 as it processes the area and take the compaction density measurements in parallel to compactor 200 processing the terrain.

Figure 3A:
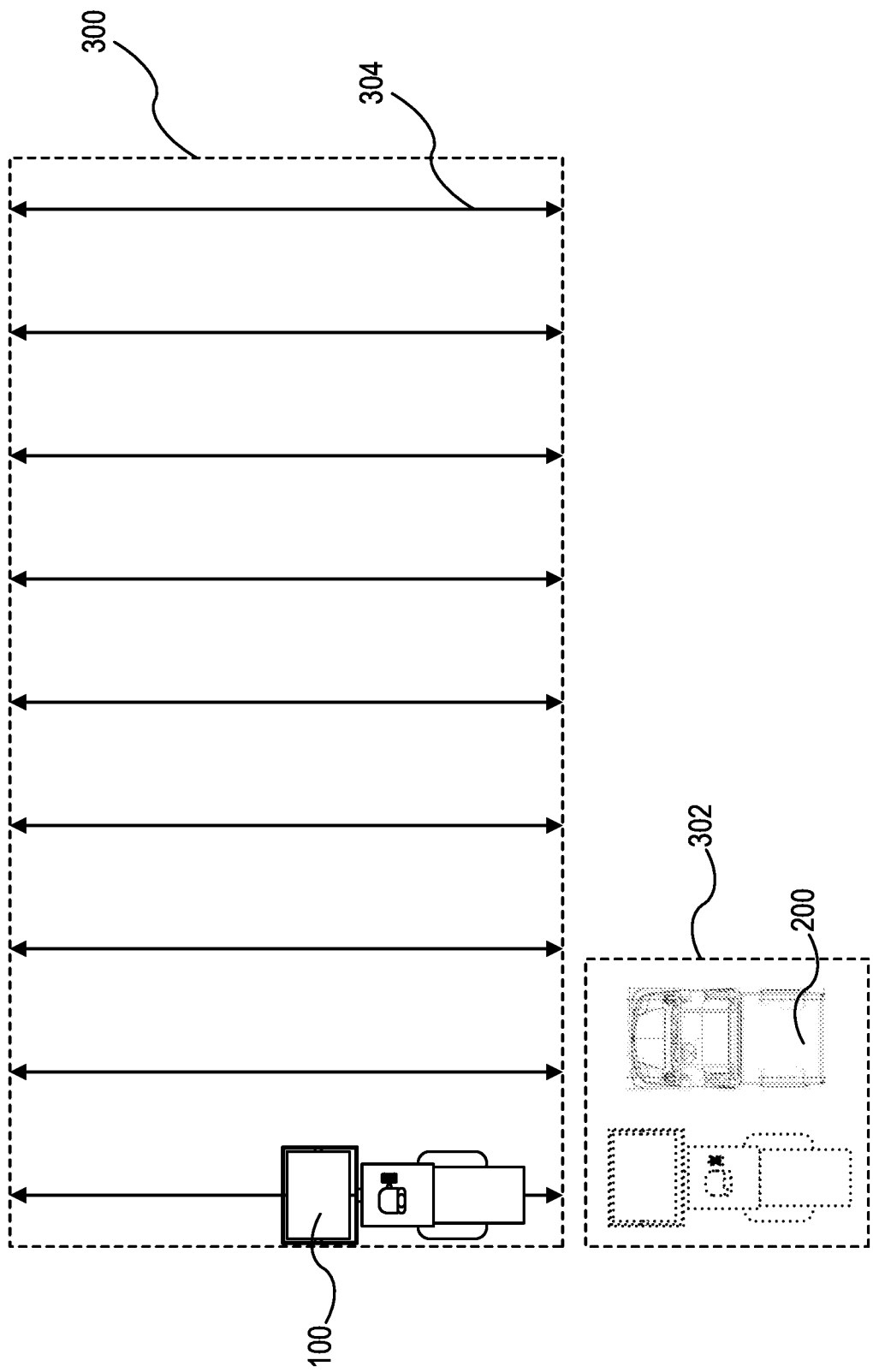
FIGS. 3A and 3B depict the compactor of FIG. 1 and the autonomous vehicle of FIG. 2 operating to compact and test an area of terrain.
Figure 3B:
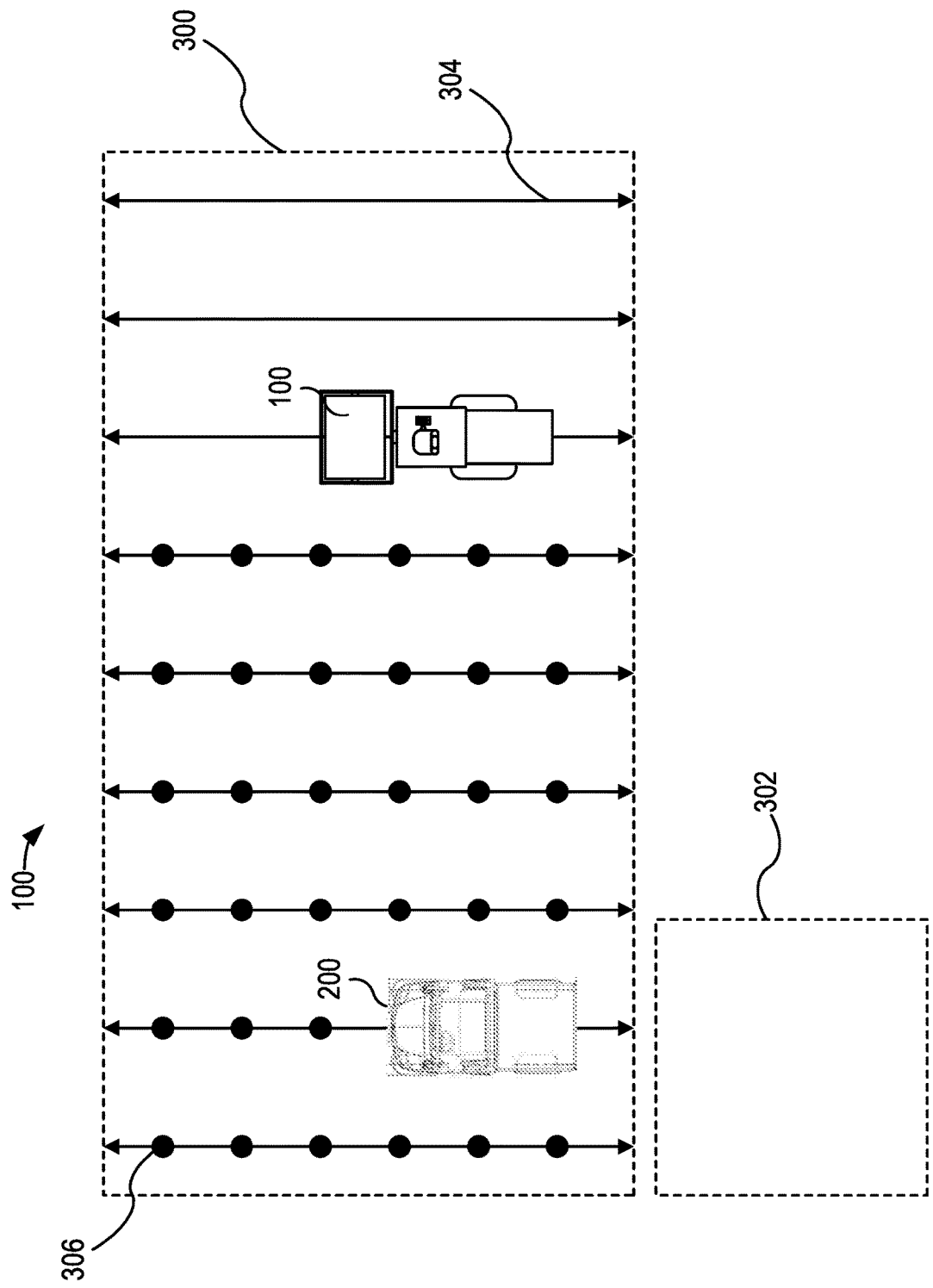

FIGS. 3A and 3B depict an example of compactor 100 and autonomous vehicle 200 processing an area of terrain 300. In the example of FIGS. 3A and 3B, compactor 100 and vehicle 200 as located in staging area 302 prior to processing and testing area 300. Compactor 100 is operated to process target area 300 by traversing the area via compaction paths 304. Compactor 100 can be operated to execute one or more passes over target area 300 and may take various paths across the terrain including paths that vary from the depicted example paths 304.

In one example, compactor 100 is manually operated by a human operator, who sits in cab 112 and can manipulate/actuate various input controls like engine throttle, steering wheel or other steering input control, joysticks or other input controls for an implement, as examples. In another example, ECU 114 and/or other ECUs of compactor 100 autonomously control operation of compactor 100 by, for example, executing one or more algorithms/programs/routines stored in memory of the ECU(s).

In FIG. 3A, compactor 100 has left staging area 302 and has commenced compacting asphalt (or another material) within area 300 and autonomous vehicle 200 remains positioned in staging area 302. In FIG. 3B, compactor 100 has completed compacting a portion of area 300 and continues traversing the remaining area to complete one or more compaction runs of the entire area. As compactor 100 is still completing processing target area 300, vehicle 200 autonomously commences testing the portion of area 300 already compacted by compactor 100. In this sense, vehicle 200 "follows" compactor 100 and tests the compacted of area 300 in parallel with compactor 100 compacting the area.

In other examples according to this disclosure, vehicle 200 (or another autonomous terrestrial vehicle in accordance with this disclosure) can begin its autonomous compaction density test run after compactor 100 has processed (e.g., compacted) all of target area 300. However, there may be advantages to vehicle 200 "following" compactor 100 as the compactor processes area 300. For example, implementing the autonomous controls of vehicle 200 may be less complex and costly where vehicle 200 is configured to follow compactor 300 (or another work machine). As an example, in such situations, the autonomous controls of vehicle 200 may not be required to know the absolute position of vehicle 200, which may simplify implementation of the controls. For example, vehicle 200 may be capable of being autonomously controlled by controlling movement of the vehicle relative to the position of compactor 100.

As an example of one such implementation where vehicle 200 follows compactor 100 as the compactor completes a compaction run, compactor 100 may come equipped with GPS or other vehicle locating system and can be configured to determine and store the location of the vehicle as it processes area 300. These locations, traversed by compactor 100, may then be transmitted by ECU 114 to controller 212 of vehicle 200 and controller 212 can be programmed to cause vehicle 200 to traverse a path including all of the locations received from ECU 114 of compactor 100.

Another potential advantage of vehicle 200 following compactor 100 as the compactor processes area 300 may be the ability to implement a closed loop control of the operation of compactor 100 based on the compaction density measurements taken autonomously by vehicle 200. For example, as compactor 100 is continuing compaction of area 300, controller 212 of vehicle 200 takes a number of compaction density measurements using meter 214 and transmits the measurements to ECU 114. ECU 114 may be configured to determine if the measurements received from controller 212 meet a target, prescribed, required or other threshold or standard for compaction density. IN the event that ECU 114 determines, for example, that measurements taken by vehicle 200 do not meet the threshold/standard, ECU 114 or another ECU or control of compactor 100 can be configured to adjust/modulate the operation of, for example, drum 110 of compactor 100 to increase compaction density of the remaining portion of area 300.

Notwithstanding potential advantages of vehicle 200 following compactor 100, in examples according to this disclosure, an autonomous terrestrial vehicle can be equipped with controls to cause the vehicle to either follow the work machine as it processes a target area of terrain or to cause the vehicle to execute its compaction density test run after the work machine has completed processing the entire target area.

Referring again to FIG. 3B, vehicle 200 is autonomously controlled by controller 212 to traverse the portion of area 300 already compacted by compactor 100 as compactor 100 continues processing the remaining portion of area 300. Controller 212, in addition to autonomously controlling movement of vehicle 200, controls compaction density meter 214 to take a plurality of compaction density measurements at a plurality of locations 306. Controller 212 is also configured to transmit the compaction density measurements and the locations at which such measurements are taken to another device/system, including sending the measurements to ECU 114 of compactor 100. In addition to transmitting compaction density measurements to ECU 114 or another ECU or control of compactor 100, controller 212 of vehicle 200 can send this and other information to other devices/systems, including, for example, a stationary or mobile base station close to or remote from compactor 100, vehicle 200, and area 300.

Vehicle 200 and controller 212 can be configured to communicate information, including compaction density measurements wirelessly with other devices/systems. For example, controller 212 of vehicle 200 can be configured to communicate wirelessly using 802.11, Bluetooth, Bluetooth Low Energy (BLE), Near Field Communication (NFC), or other radio frequencies and/or using other standard and/or proprietary frequencies and/or protocols.

Figure 4:
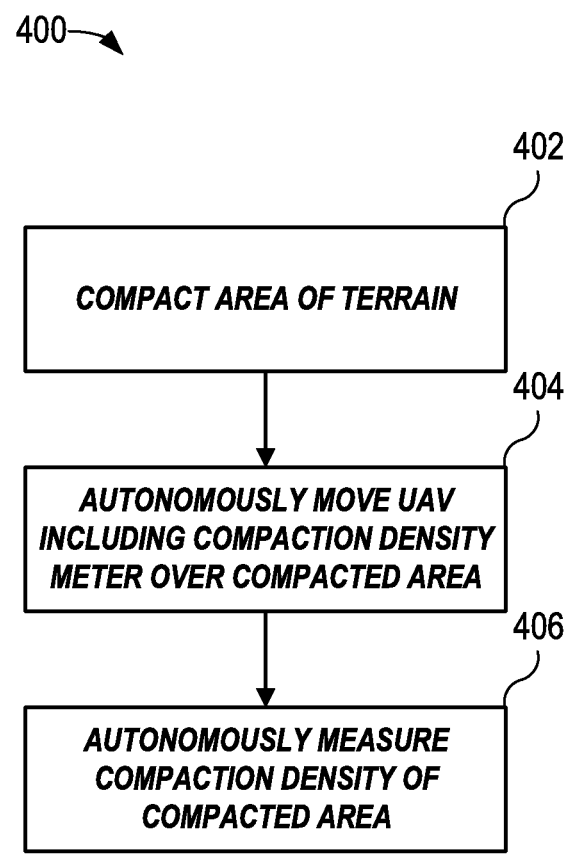
FIG. 4 is a flowchart depicting an example method of processing and testing an area of terrain in accordance with this disclosure.

FIG. 4 is a flowchart depicting an example method of processing a target area of terrain in accordance with this disclosure. In FIG. 4, method 400 includes compacting at least a portion of an area of terrain with a compactor work machine (402), moving, by a controller, an unmanned autonomous vehicle (UAV) over the at least a portion of the compacted area (404), and autonomously measuring, by the controller, a compaction density of the at least a portion of the compacted area at one or more locations with a compaction density meter coupled to the UAV and communicatively coupled to the controller (406). The example method can be executed using, as an example, compactor 100 including ECU 114 and autonomous vehicle 200 including controller 212 and compaction density meter 214. Additionally, example method can be executed using different work machines and/or different UAVs in accordance with this disclosure.

The method of FIG. 4 can also include autonomously sending, by the controller of the UAV, information indicative of the compaction density measurements at the one or more locations to another device close to or remote from the vehicle. In an example, the UAV controller can send the compaction density measurements and measurement locations to the compactor machine or a controller thereof.

In an example, the controller of the UAV is configured to control movement of the vehicle and to control the compaction density meter to take the plurality of compaction density measurements at the plurality of locations after the compactor work machine has compacted all of the area of terrain. In another example, the controller of the UAV is configured to control movement of the vehicle and to control the compaction density meter to take the plurality of compaction density measurements at the plurality of locations before the compactor work machine has compacted all of the area of terrain. In other words, the UAV and the controller(s) thereof may be configured to autonomously test compaction density of a target area in parallel with a compactor machine compacting the area.

In instances in which the controller of the UAV is configured to control movement of the vehicle and to control the compaction density meter to take the plurality of compaction density measurements at the plurality of locations before the compactor work machine has compacted all of the area of terrain, the controller of the UAV can be configured to autonomously send the plurality of compaction density measurements and the plurality of locations to a controller of the compactor work machine, and the controller of the compactor can be configured to compare the plurality of compaction density measurements to one or more thresholds. Additionally, the controller of the compactor can modulate operation of an implement, for example, a vibratory drum implement based on the comparison of the plurality of compaction density measurements to the one or more thresholds.

INDUSTRIAL APPLICABILITY

In an example in accordance with this disclosure, an operator operates a drum compactor to process an area of material and a UAV automatically tests the compaction density of the area processed by the compactor. In an example, a compactor work machine and autonomous terrestrial vehicle work in concert to compact and test an area of asphalt. Compaction density standards or thresholds may be required by local city, county or state and/or federal regulations. In order to comply with such regulations, processing a target area of terrain, e.g., compacting an area of asphalt may require an additional step of measuring compaction density after one or more compaction runs by a compactor machine.

Such compaction density measurements have commonly been executed manually by an operator positioning a compaction density meter at various locations of an area of terrain that has already been compacted and taking measurements and then comparing the measurements to thresholds or standards for compacted asphalt or other materials. In examples according to this disclosure, however, an autonomous vehicle is configured to automatically traverse an area of terrain that has been or is in the process of being compacted and to automatically take a plurality of compaction density measurements and, optionally transmit the measurements to another device or system, including, as examples, a stationary or mobile base station or another vehicle like the compactor machine associated with the autonomous vehicle. In examples, the UAV can be configured to take the compaction density measurements with a compaction density meter coupled thereto and can sample and send the measurements after the target area of asphalt has been completely compacted by the compactor, or, alternatively, the UAV can follow the compactor as it processes the area and take the compaction density measurements in parallel to the compactor compacting the area of asphalt.

In one example, the compactor is manually operated by a human operator, who sits in a cab of the compactor and who can manipulate/actuate various input controls like engine throttle, steering wheel or other steering input control, joysticks or other input controls for an implement, as examples. The UAV is controlled by a controller thereof to traverse the portion of area already compacted by the compactor, either before or after the compactor has completed compacting all of the area of asphalt. The UAV controller, in addition to autonomously controlling movement of the UAV, controls a compaction density meter to take a plurality of compaction density measurements at a plurality of locations of the target area. The UAV controller is also configured to transmit the compaction density measurements and the locations at which such measurements are taken to another device/system, including sending the measurements to a controller of the compactor.

Various examples are illustrated in the figures and foregoing description. One or more features from one or more of these examples may be combined to form other examples.

The above detailed description is intended to be illustrative, and not restrictive. The scope of the disclosure should, therefore, be determined with references to the appended claims, along with the full scope of equivalents to which such claims are entitled.

What is claimed is:

1. An autonomous terrestrial compaction testing vehicle comprising:
    a compaction density meter coupled to the autonomous terrestrial compaction testing vehicle and configured to take a plurality of compaction density measurements when the autonomous terrestrial compaction testing vehicle is physically on terrain; and
    a controller communicatively connected to the compaction density meter and to a compactor machine that is compacting an area of the terrain, the controller configured to autonomously:
    control movement of the autonomous terrestrial compaction testing vehicle over the compacted area; and
    control the compaction density meter to take the plurality of compaction density measurements at a plurality of locations of the compacted area,
    wherein the controller is configured to control movement of the autonomous terrestrial compaction testing vehicle along the terrain and to control the compaction density meter to take the plurality of compaction density measurements at the plurality of locations before the compactor machine has compacted all of the area of the terrain, and
    wherein the movement of the autonomous terrestrial compaction testing vehicle under the control of the controller is such that the autonomous terrestrial compaction testing vehicle follows a route the compactor machine has taken to compact the area of the terrain based on location data received from the compactor machine.

2. The vehicle of claim 1, wherein the controller is configured to autonomously send the plurality of compaction density measurements and the plurality of locations to another device remote from the autonomous terrestrial compaction testing vehicle.

3. The vehicle of claim 2, wherein the controller is configured to autonomously send the plurality of compaction density measurements and the plurality of locations to the compactor machine.

4. The vehicle of claim 3, wherein the controller is configured to autonomously send the plurality of compaction density measurements and the plurality of locations to a controller of the compactor machine.

5. The vehicle of claim 1, wherein the compaction density measurements taken by the compaction density meter of the autonomous terrestrial compaction testing vehicle are physical measurements of the terrain using a mechanical or electromechanical device that physically contacts the terrain to perform the compaction density measurements.

6. The vehicle of claim 1, wherein the location data received from the compactor machine is received in real time as the compactor machine compacts the area of the terrain.

7. A system comprising:
    a compactor work machine comprising a compactor controller and configured to compact an area of terrain; and
    a land-based unmanned autonomous vehicle (UAV) comprising:
    a compaction density meter coupled to the UAV; and
    a UAV controller communicatively connected to the compaction density meter and to the compactor controller, the UAV controller configured to autonomously:
    control movement of the UAV over at least a portion of the area of the terrain that has been compacted by the compactor work machine; and
    control the compaction density meter to take a plurality of compaction density measurements at a plurality of locations of the area of the terrain that have been compacted,
    wherein the compactor controller is configured to control the compactor work machine based on a closed loop control using feedback from the UAV controller regarding the compaction density measurements as the compaction density meter takes compaction density measurements at the plurality of locations of the area of the terrain that have been compacted by the compactor work machine.

8. The system of claim 7, wherein the UAV controller is configured to autonomously send the plurality of compaction density measurements and the plurality of locations to another device remote from the UAV.

9. The system of claim 7, wherein the UAV controller is configured to autonomously send the plurality of compaction density measurements and the plurality of locations to the compactor work machine.

10. The system of claim 9, wherein the UAV controller is configured to autonomously send the plurality of compaction density measurements and the plurality of locations to the compactor controller.

11. The system of claim 7, wherein the UAV controller is configured to control movement of the UAV on the terrain and to control the compaction density meter to take the plurality of compaction density measurements at the plurality of locations after the compactor work machine has compacted all of the area of the terrain.

12. The system of claim 7, wherein the UAV controller is configured to control movement of the UAV on the terrain and to control the compaction density meter to take the plurality of compaction density measurements at the plurality of locations before the compactor work machine has compacted all of the area of the terrain.

13. The system of claim 12,
    wherein the UAV controller is configured to autonomously send the plurality of compaction density measurements and the plurality of locations to the compactor controller, and
    wherein the compactor controller is configured to compare the plurality of compaction density measurements to one or more thresholds.

14. The system of claim 13, wherein the compactor controller is configured to modulate operation of an implement of the compactor work machine based on the comparison of the plurality of compaction density measurements to the one or more thresholds.

15. A method comprising:
    moving, by a controller, an unmanned autonomous vehicle (UAV) over at least a portion of an area of terrain known to have been compacted by a compactor work machine; and
    autonomously physically measuring, under control of the controller of the UAV, a compaction density of the at least the portion of the area of the terrain known to have been compacted by the compactor work machine at one or more locations with a compaction density meter coupled to the UAV and communicatively coupled to the controller,
    wherein said moving the unmanned autonomous vehicle is according to a predetermined route identified to have been taken by the compactor work machine to compact at least the portion of the area of the terrain.

16. The method of claim 15, further comprising autonomously sending, by the controller, information indicative of the compaction density measurements at the one or more locations to another device close to or remote from the UAV.

17. The method of claim 15, further comprising autonomously sending, by the controller, information indicative of the compaction density measurements at the one or more locations to the compactor work machine.

18. The method of claim 17, wherein autonomously sending comprises autonomously sending, by the controller, information indicative of the compaction density measurements at the one or more locations to a second controller of the compactor work machine.

19. The method of claim 15, wherein the controller of the UAV is configured to control movement of the vehicle and to control the compaction density meter to take the plurality of compaction density measurements at the plurality of locations after the compactor work machine has compacted all of the area of terrain.

20. The method of claim 15, wherein the controller of the UAV is configured to control movement of the vehicle and to control the compaction density meter to take the plurality of compaction density measurements at the plurality of locations before the compactor work machine has compacted all of the area of terrain.

21. The method of claim 20,
wherein the controller of the UAV is configured to autonomously send the plurality of compaction density measurements and the plurality of locations to a second controller of the compactor work machine, and
wherein the second controller is configured to compare the plurality of compaction density measurements to one or more thresholds.

22. The method of claim 21, wherein the second controller is configured to modulate operation of an implement of the compactor work machine based on the comparison of the plurality of compaction density measurements to the one or more thresholds.

* * * * *